(12) United States Patent
McPherson et al.

(10) Patent No.: US 8,657,808 B2
(45) Date of Patent: Feb. 25, 2014

(54) SURGICAL APPARATUS INCLUDING A HAND-ACTIVATED, CABLE ASSEMBLY AND METHOD OF USING SAME

(75) Inventors: Cameron McPherson, Frisco, TX (US); Rex W. Shores, Norfolk, MA (US); Mitchell Sherry, Fort Worth, TX (US)

(73) Assignee: Medtronic, Inc., Minneapolis, MN (US)

( * ) Notice: Subject to any disclaimer, the term of this patent is extended or adjusted under 35 U.S.C. 154(b) by 1591 days.

(21) Appl. No.: 10/930,646

(22) Filed: Aug. 31, 2004

(65) Prior Publication Data
US 2006/0047271 A1 Mar. 2, 2006

(51) Int. Cl.
*A61B 17/00* (2006.01)

(52) U.S. Cl.
USPC ................................. 606/1; 606/34

(58) Field of Classification Search
USPC .................... 324/67; 606/1, 34, 170
See application file for complete search history.

(56) References Cited

U.S. PATENT DOCUMENTS

| | | | |
|---|---|---|---|
| 4,835,509 A | 5/1989 | Yoshino et al. | |
| 5,136,220 A | 8/1992 | Philipp | |
| 5,365,155 A | 11/1994 | Zimmermann | |
| 5,690,618 A * | 11/1997 | Smith et al. | 604/232 |
| 5,712,543 A | 1/1998 | Sjostrom | |
| 5,720,742 A * | 2/1998 | Zacharias | 606/1 |
| 5,867,082 A | 2/1999 | Van Zeeland | |
| 6,017,354 A * | 1/2000 | Culp et al. | 606/170 |
| 6,520,976 B1 * | 2/2003 | Gage | 606/170 |
| 7,247,161 B2 * | 7/2007 | Johnston et al. | 606/170 |
| 2001/0007944 A1 * | 7/2001 | Mark et al. | 606/170 |
| 2002/0087179 A1 | 7/2002 | Culp et al. | |
| 2004/0172015 A1 * | 9/2004 | Novak | 606/34 |
| 2005/0096661 A1 * | 5/2005 | Farrow et al. | 606/79 |
| 2006/0020258 A1 * | 1/2006 | Strauss et al. | 606/1 |
| 2006/0047272 A1 * | 3/2006 | McPherson et al. | 606/1 |

FOREIGN PATENT DOCUMENTS

| | | |
|---|---|---|
| DE | 2820437 | 7/1979 |
| JP | 2002345843 | 12/2002 |
| WO | WO 99/20187 | 3/1999 |
| WO | WO 03/079911 | 10/2003 |

OTHER PUBLICATIONS

European Examination Report issued Jun. 26, 2007 by Philip Nice, Primary Examiner for the Examining Division, in application No. 05 009 372.3-1526.

* cited by examiner

*Primary Examiner* — S. Thomas Hughes
*Assistant Examiner* — Sarah Simpson
(74) *Attorney, Agent, or Firm* — Harness, Dickey

(57) ABSTRACT

A surgical apparatus and method according to which a cable assembly is connected to a handpiece and includes a sensing element, and a member adapted to move relative to the sensing element to control the operation of a motor in the handpiece.

26 Claims, 2 Drawing Sheets

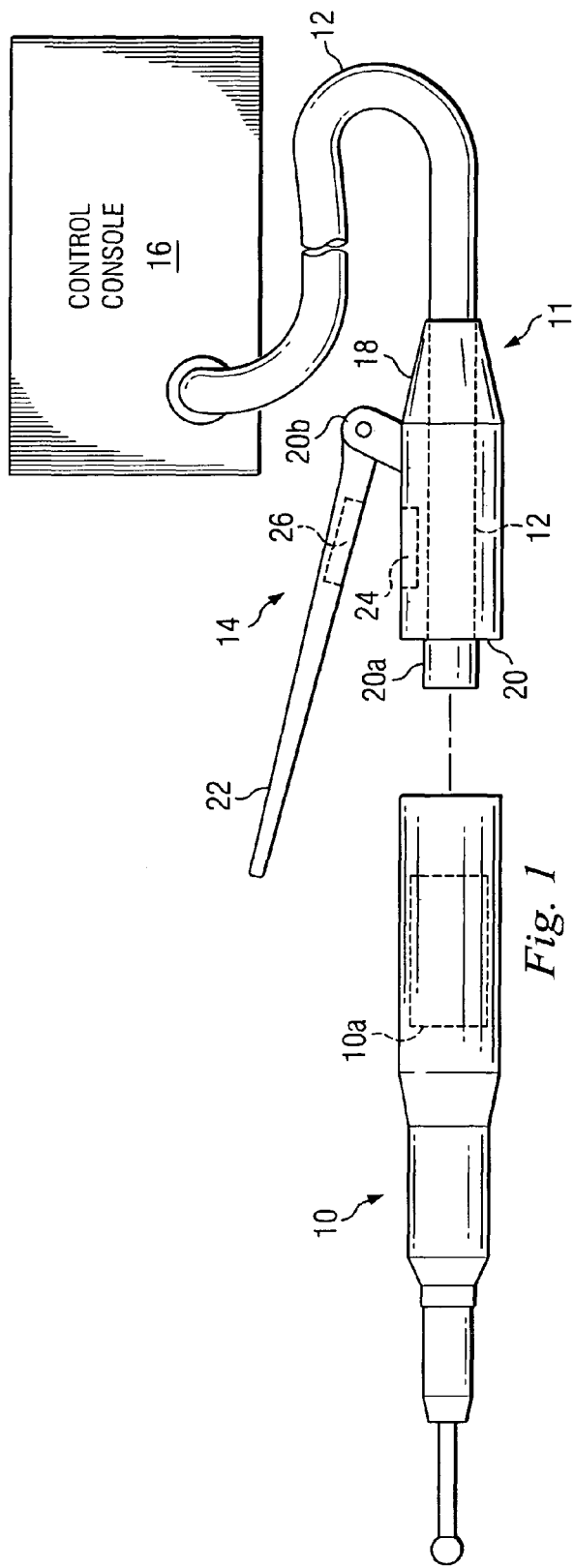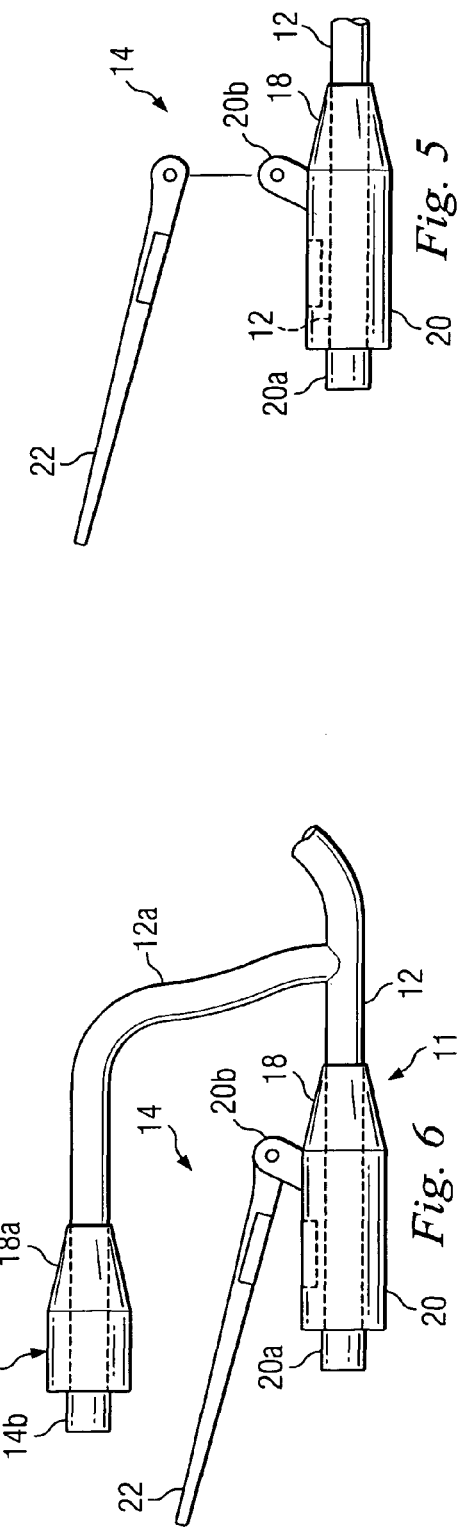

SURGICAL APPARATUS INCLUDING A HAND-ACTIVATED, CABLE ASSEMBLY AND METHOD OF USING SAME

FIELD OF THE INVENTION

This invention relates to a surgical apparatus including a hand-activated, cable assembly, and to a method of using same.

BACKGROUND

Many tools for use in surgical procedures take the form of a handpiece driven by an electric motor to which a cutting accessory, such as a drill bit, bur, saw blade, reamer, and the like, is attached, for removing or separating sections of body tissue.

A hand-activated control switch is usually provided on the handpiece and a sensing element is provided in the handpiece and cooperates with the switch to generate a signal representative of the position of the switch. The signal is sent to a console that converts the available line voltage into a voltage signal and sends the signal to the motor of the handpiece to power the motor.

However, these types of arrangements are not without limitations. For example, if the sensing element within the handpiece fails prematurely, then hand-activation of the handpiece is not possible until it is repaired. Also, the switch is designed to work with only those handpieces that have a sensing element in the handpiece, and handpieces that do not have an imbedded sensing element cannot be used with a hand-activated control switch. Moreover, if the sensing element is in the form of a Hall-effect sensing element that detects the proximity of a magnet in or on the lever, the sensing element could be inadvertently activated if the handpiece were placed on or near a magnet or a magnetic surface.

The publication listed in Table 1 below is hereby incorporated by reference herein in its entirety. As those of ordinary skill in the art will appreciate readily upon reading the Summary of the Invention, Detailed Description of the Preferred Embodiments and Claims set forth below, many of the devices and methods disclosed in the publication of Table 1 may be modified advantageously by using the teachings of the present invention.

TABLE 1

| Patent/Publication No. | Published Date | Inventor |
| --- | --- | --- |
| 2002/0087179 A1 | Jul. 4, 2002 | Jerry A. Culp, et al. |

SUMMARY

In order to overcome the above problems, and according to an embodiment of the present invention, a surgical apparatus is provided that includes a sensing element and a switch incorporated in a cable assembly that connects to a handpiece and to a console. The cable assembly can be used with a variety of handpieces, and, if the sensing element fails prematurely, the handpiece is not rendered inoperable, but rather the cable assembly can simply be replaced with a new one. Also, a Hall-effect sensing element can be used without running the risk of inadvertently activating the sensing element if the handpiece were placed on or near a magnet or a magnetic surface.

Various embodiments of the invention discussed below may possess one or more of the above features and advantages, or provide one or more solutions to the above problems.

BRIEF DESCRIPTION OF THE DRAWINGS

FIG. 1 is an exploded isometric view of an embodiment of the present invention.

FIGS. 3-6 are views similar to that of FIG. 2 but depicting alternate embodiments of the component of FIG. 2.

DETAILED DESCRIPTION

Figure 2:
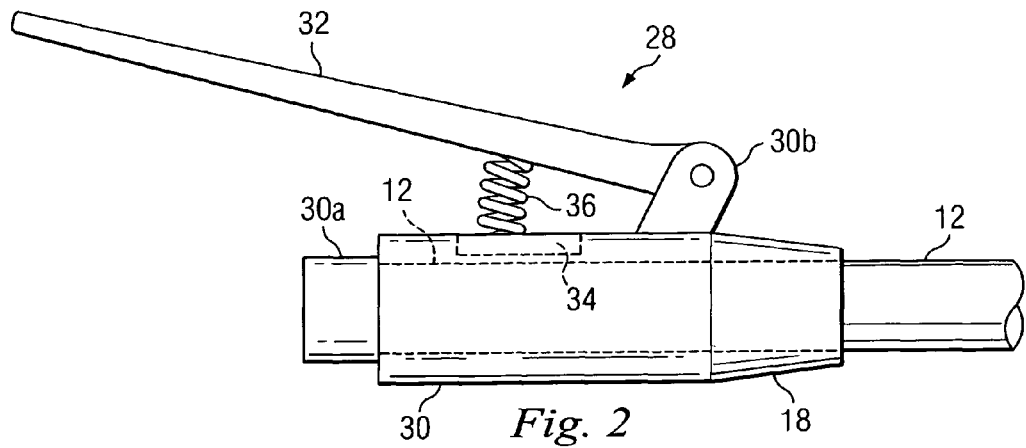
FIG. 2 is an enlarged elevational view of a component of the embodiment of FIG. 1.

Referring to FIG. 1 of the drawings, the reference 10 refers, in general, to a handpiece in the form of a powered tool for use in surgical procedures. The handpiece 10 is driven by an internal motor 10a, and is adapted to receive a cutting accessory, such as a drill bit, a bur, a saw blade, a reamer, or the like, that can be removably connected to the output shaft of the motor 10a. When the motor 10a is activated in a manner to be described, the output shaft and therefore the cutting accessory are rotated at a predetermined speed for removing or separating sections of body tissue.

A cable assembly 11 is provided that includes a cable 12, one end of which is electrically and mechanically connected to the handpiece 10 in a manner to be described. The cable assembly 11 also includes a switch/sensing element device 14 extending over the latter end portion and adapted to be activated and to control the handpiece 10, also in a manner to be described.

The other end of the cable 12 is electrically and mechanically connected to a console 16 that contains electrical circuitry that converts the available line voltage into a drive signal suitable for driving the motor 10a. A conventional, conically-shaped, strain relief sleeve 18 extends from the device 14 and over the corresponding portion of the cable 12.

The device 14, when manually actuated under conditions to be described, produces signals that are transmitted, via the cable 12, to the console 16. The console 16 responds to these signals and, in turn, produces the above drive signals that are transmitted to the motor 10a, via the cable 12, and through the device 14 to the motor 10a.

The device 14 includes a cylindrical housing 20 that extends around the corresponding end portion of the cable 12. A male electrical plug, or jack, 20a extends from one end of the housing 20 and is connected to the corresponding end of the cable 12 and engages a corresponding female socket (not shown) provided in the corresponding end of the handpiece 10 (FIG. 1). It is understood that the cable 12 includes one or more electrical conductors that extend into the other end of the housing 20 and are connected in a manner to be described.

The device 14 also includes a lever 22 pivotally mounted between two spaced mounting flanges extending from the housing 20, with one of the flanges being referred to by the reference numeral 20b. It is understood that a biasing member (not shown), such as a leaf spring or the like, can be provided that biases the lever in a direction away from the housing 20 and provides resistance to movement towards the housing, in a conventional manner.

A Hall-effect sensing element 24 is disposed in the housing 20 with the upper surface of the sensing element extending flush with the upper surface of the housing, as viewed in FIG. 2. A magnet 26 is provided in the lever 22 in alignment with the sensing element 24, with the lower surface of the magnet extending flush with the lower surface of the lever. The sensing element 24 is conventional and, as such, responds to movement of the lever 22, and therefore the magnet 26, proximate to the sensing element, and outputs a corresponding signal, as will be described in detail. When the lever 22 is released, the above-mentioned leaf spring forces it back to its original position.

The cable 12 (FIG. 1) contains a plurality of electrical conductors (not shown) that are electrically connected to the console 16 and extend from the console to the housing 20, where one or more of the conductors are electrically connected to the sensing element 24 in the housing 20 and one or more are electrically connected to the jack 20a of the housing for connection to the motor 10a. Thus, a signal emitted by the sensing element 24 is transmitted to the console 16, causing a drive signal to be transmitted from the console to the motor 10a to drive the motor. Preferably the latter signal is in the form of a DC voltage that can vary, depending on the position of the magnet relative to the sensing element, to enable the speed of the motor 10a to be varied accordingly.

In operation, the surgeon attaches a cutting tool to the handpiece 10 and uses his finger to manually push, or force, the lever 22 towards the housing 20 so that the magnet 26 approaches the sensing element 24. The sensing element 24 is calibrated to output a signal when the magnet 26 gets within a predetermined distance of the sensing element, and the signal is transmitted to the console 16, via the corresponding conductors in the cable 12.

The above-mentioned electrical circuitry in the console 16 responds to the signal received from the device 14, and generates a signal that is passed to the motor 10a, via the corresponding conductors in the cable 12. The signal drives the motor 10a and enables the speed of the motor to be varied, depending on the position of the magnet relative to the sensing element 24, as discussed above.

An alternate embodiment of the device 14 is referred to, in general, by the reference numeral 28 in FIG. 2 and includes a housing 30 having a male electrical plug, or jack, 30a extending from one end thereof that mechanically and electrically engages a corresponding female socket (not shown) provided in the corresponding end of the handpiece 10 (FIG. 1). It is understood that the cable 12 includes one or more electrical conductors that extend into the other end of the housing 30 and are connected in a manner to be described. The device 28 also includes a lever 32 is pivotally mounted between two spaced mounting flanges extending from the housing 30, with one of the flanges being referred to by the reference numeral 30b.

A strain gauge 34 is disposed in the housing 30 with the upper surface of the strain gauge extending flush with the upper surface of the housing, as viewed in FIG. 2. The strain gauge 34 is conventional and, as such, is calibrated to respond to a predetermined force exerted on it and to output a corresponding signal, as will be described in detail.

A helical compression spring 36 extends between the latter surface and the upper surface of the strain gauge 34 so as to normally urge the lever away from the housing 30. When the lever 32 is manually pivoted towards the housing 30, it exerts a force on the spring 36, which compresses the spring and, in turn, exerts a force on the strain gauge 34. When the lever 32 is released, the spring forces it back to its original position.

The cable 12 (FIG. 1) contains a plurality of electrical conductors (not shown) that are electrically connected to the console 16 and extend from the console to the housing 30, where one or more of the conductors are electrically connected to the sensing element strain gauge 34 in the housing 30, and one or more are electrically connected to the jack 30a of the housing for connection to the motor 10a. Thus, a signal emitted by the strain gauge 34 is transmitted to the console 16, causing a signal to be transmitted from the console to the motor 10a to drive the motor. Preferably the latter signal is in the form of a DC voltage that can vary, depending on the force exerted on the strain gauge 34, to enable the speed of the motor 10a to be varied accordingly.

In operation, the surgeon attaches a cutting tool to the handpiece 10 and uses his finger to manually push, or force, the lever 32 towards the housing 30 against the force of the spring 36 so that a corresponding force is exerted on the strain gauge 34. The strain gauge 34 is calibrated to output a signal when the latter force reaches a predetermined value, and the signal is transmitted to the console 16, via the corresponding conductors in the cable 12.

The above-mentioned electrical circuitry in the console 16 responds to the signal received from the device 14, and generates a signal that is passed to the motor 10a, via the corresponding conductors in the cable 12. The signal drives the motor and enables the speed of the motor to be varied, depending on the force exerted on the strain gauge 34, as discussed above.

Figure 3:
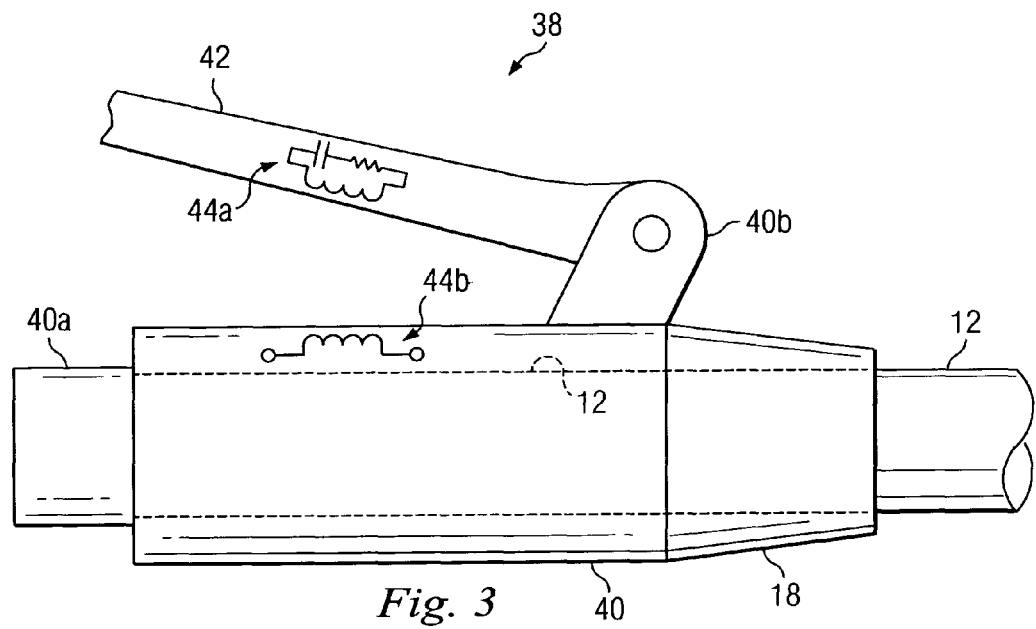

Another alternate embodiment of the device 14 is referred to, in general, by the reference numeral 38 in FIG. 3 and includes a housing 40 having a male electrical plug, or jack, 40a extending from one end thereof that mechanically and electrically engages a corresponding female socket (not shown) provided in the corresponding end of the handpiece 10 (FIG. 1). It is understood that the cable 12 includes one or more electrical conductors that extend into the other end of the housing 40 and are connected in a manner to be described.

The device 38 also includes a lever 42 pivotally mounted between two spaced mounting flanges extending from the housing 40, with one of the flanges being referred to by the reference numeral 40b. It is understood that a biasing member (not shown), such as a leaf spring or the like, can be provided that biases the lever 42 in a direction away from the housing 40 and provides resistance to movement towards the housing in a conventional manner.

One portion 44a of an inductively coupled circuit is mounted in the lever 42 and another portion 44b of the circuit is mounted in the housing 40 and in alignment with the circuit portion 44a. The circuit portion 44a is in the form of a resonant circuit (RLC) and the circuit portion 44b includes an inductor. Thus, the circuit portion 44a interacts with the circuit portion 44b to induce an output signal voltage in the circuit portion 44b when the circuit portion 44a is within a predetermined distance of the circuit portion 44b as a result of the lever 42 being pivoted towards the housing 40. When the lever 42 is released, the above-mentioned leaf spring forces it back to its original position.

The cable 12 (FIG. 1) contains a plurality of electrical conductors (not shown) that are electrically connected to the console 16 and extend from the console to the housing 40, where one or more of the conductors are electrically connected to the circuit 44b in the housing 20, and one or more are electrically connected to the jack 40a of the housing for connection to the motor 10a. Thus, a signal emitted by the assembly 38 in the above manner is transmitted to the console 16, causing a signal to be transmitted from the console to the handpiece motor 10a to drive the motor. Preferably the latter signal is in the form of a DC voltage that can vary, depending on the relative positions of the circuit portions 44a and 44b, to enable the speed of the motor 10a to be varied accordingly.

In operation, the surgeon attaches a cutting tool to the handpiece 10 and uses his finger to manually push, or force, the lever 42 towards the housing 40. The inductively coupled circuit portions 44a and 44b are calibrated to output a signal when the lever 42, and therefore the circuit portion 44a, gets within a predetermined distance of the circuit portion 44b in the housing 40, and the signal is transmitted to the console 16, via the corresponding conductors in the cable 12.

The above-mentioned electrical circuitry in the console 16 responds to the signal received from the device 14, and generates a signal that is passed to the motor 10a, via the corresponding conductors in the cable 12. The signal drives the motor 10 and enables the speed of the motor to be varied, depending on the relative positions of the circuit portions 44a and 44b, as discussed above.

Figure 4:
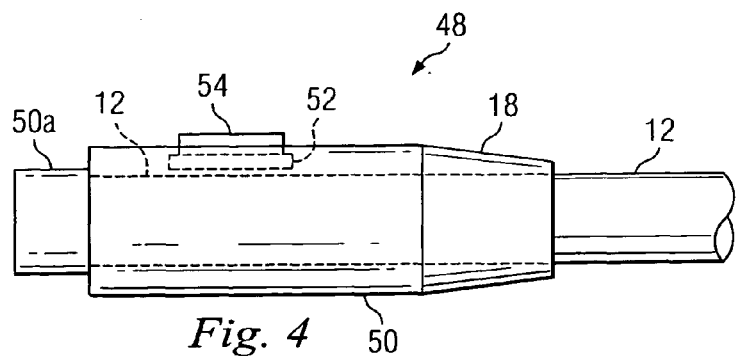

Another alternate embodiment of the device 14 is referred to, in general, by the reference numeral 48 in FIG. 4 and includes a housing 50 having a male electrical plug, or jack, 50a extending from one end thereof that mechanically and electrically engages a corresponding female socket (not shown) provided in the corresponding end of the handpiece 10 (FIG. 1). It is understood that the cable 12 includes one or more electrical conductors that extend into the other end of the housing 30 and are connected in a manner to be described.

The device 14 also includes a strain gauge 52 disposed in an opening in the housing 50 with the upper surface of the strain gauge extending slightly below the upper surface of the housing, as viewed in FIG. 5. The lower portion of a manually-actuatable button 54 also extends in the latter opening over the strain gauge 52, with the lower surface of the button in contact with the upper surface of the strain gauge 52. The upper portion of the button 54 projects outwardly from the upper surface of the housing 50 so that it can be manually engaged, or pressed.

The strain gauge 52 is conventional and, as such, responds to a force exerted on it by a manual pressing of the button 54 downwardly as viewed in the drawing, and is calibrated to output a corresponding output signal. In this context, it is understood that the button 54 is conventional, and, as such, includes a mechanism to return it to its previous position after being pushed downwardly in the above manner.

The cable 12 (FIG. 1) contains a plurality of electrical conductors (not shown) that are electrically connected to the console 16 and extend from the console to the housing 50, where one or more of the conductors are electrically connected to the strain gauge 52 in the housing 50 and one or more are electrically connected to the jack 50a of the housing for connection to the motor 10a. Thus, a signal emitted by the assembly 48 in the above manner is transmitted to the console 16, causing a signal to be transmitted from the console to the handpiece motor 10a to drive the motor. Preferably the latter signal is in the form of a DC voltage that can vary, depending on the position of the magnet relative to the sensing element, to enable the speed of the motor 10a to be varied accordingly.

In operation, the surgeon attaches a cutting tool to the handpiece 10 and uses his finger to manually push or force the button 54 towards the strain gauge 52 to exert a force on the strain gauge 52. The strain gauge 52 is calibrated to output a signal when the latter force reaches a predetermined value, and the signal is transmitted to the console 16, via the corresponding conductors in the cable 12.

The above-mentioned electrical circuitry in the console 16 responds to the signal received from the device 14, and generates a drive signal that is passed to the motor 10a, via the corresponding conductors in the cable 12. The signal drives the motor 10a and enables the speed of the motor to be varied, depending on the amount of force exerted on the strain gauge 52 by the button 54.

It is understood that the embodiments of FIG. 1 can be modified according to FIG. 5, in which the lever is removable from its pivotal engagement between the flanges, including the flange 20b, on the housing 20. This can be done in any conventional manner such as by providing a pin (not shown) that can be inserted through aligned openings in the flanges and the lever to provide the pivotal connection, yet can be quickly removed to permit removal of the lever. This enables the surgeon to eliminate the finger control capability provided by the device 14.

It is understood that the levers 32 and 42 of the embodiments of FIGS. 3 and 4, respectively, can also be removable in the above manner.

The embodiment of FIG. 6 also provides the surgeon the option of eliminating the finger control capability provided by the device 14. In this embodiment the end portion of the cable 12 is bifurcated to form an additional portion 12a, and a male electrical plug, or jack, 58 is affixed to the end of the latter portion that mechanically and electrically engages a corresponding female socket (not shown) provided in the corresponding end of the handpiece 10 (FIG. 1). A strain relief sleeve 18a, identical to the sleeve 18, is provided that extends from the jack 58 and over the corresponding portion of the cable portion 12a.

Thus, if the surgeon wants finger control capability of the motor 10a, he can plug the jack 20a of the housing 20 into the handpiece 10 in the manner discussed above; or, if not, he can plug the jack 58 into the handpiece.

It is understood that the cable portion 12a can also be provided in the embodiments of FIGS. 2-5.

Since, in each of the above embodiments the sensing element and switch are both incorporated in the cable assembly 11, the cable assembly can be used with a variety of handpieces. Also, if the sensing element fails prematurely, the handpiece is not rendered inoperable, but rather the cable assembly 11 can simply be replaced with a new one. Further, in the embodiment of FIG. 2 there is no risk of inadvertently activating the sensing element 24 if the handpiece were placed on or near a magnet or a magnetic surface.

Variations

It is understood that several variations may be made in the foregoing without departing from the scope of the invention. For example, the levers and the push button in the above embodiments are interchangeable and could be replaced by toggle switches or finger/button interfaces. Further, sensing elements other than the ones described above can also be used. Moreover, the console can be eliminated if it is not necessary to house the above-described electrical circuit. Also, the output shaft of the motor 10a can be oscillated, reciprocated, or the like, rather than rotated, as discussed above. Moreover, the motor 10a can be in the form of a pneumatic motor, or the like.

The preceding specific embodiments are illustrative of the practice of the invention. It is to be understood that other expedients, known to those skilled in the art or disclosed herein, may be employed without departing from the invention or the scope of the appended claims. For example, the present invention is not limited to surgical instruments employing a cutting element, but may find further applications in which a relatively small instrument is powered from an external console.

In the following claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. A surgical apparatus, comprising:
a handpiece having a first housing to be grasped by a user, wherein the first housing encloses at least a motor that is configured to operate a surgical tool received by the handpiece;
a control separate and spaced apart from the handpiece, wherein the control is configured to receive a first position signal and generate a second control signal for the motor; and
a cable assembly separate from the handpiece and the control, wherein the cable assembly is configured to be selectively and removably connected to the handpiece, the cable assembly further comprising:
 a sensing element to generate the first position signal;
 at least one electrical conductor configured to transmit the first position signal and the second control signal;
 a second housing having a wall surrounding the at least one electrical conductor and the sensing element, the second housing integrated with the cable assembly while configured to be selectively and removably connected to the handpiece, wherein the at least one conductor extends through the second housing and along a cable body away from the second housing;
 a switch member configured to be connected to and moveable relative the second housing, wherein the switch member is configured to be moved by manual operation of the user; and
 a signaling member fixed relative to the switch member and moveable with the switch member relative to the sensing element surrounded by the second housing;
wherein the sensing element, surrounded by the second housing, is positioned between the motor in the handpiece and the control when the cable assembly is selectively connected to the handpiece and the control, wherein the sensing element is configured to generate the first position signal based at least on a position of the signaling member relative to the sensing element.

2. The surgical apparatus of claim 1, wherein when the cable assembly is selectively disconnected from the handpiece, the switch member is disconnected from the handpiece.

3. The surgical apparatus of claim 2, wherein the first housing includes a first connection portion configured to connectingly engage a second connection portion of the second housing.

4. The surgical apparatus of claim 3, wherein the first connection portion is a female socket and the second connection portion is a male member extending from the second housing.

5. The surgical apparatus of claim 1, wherein the switch member is pivotal relative to the second housing separate from the handpiece.

6. The surgical apparatus of claim 1, wherein the sensing element is at least one of a Hall Effect Sensor, a strain gauge, or an inductive coupled circuit.

7. The surgical apparatus of claim 1, wherein the switch member includes a first portion of an inductive coupled circuit and the sensing element is a second portion of the inductive coupled circuit.

8. The surgical apparatus of claim 1, wherein the cable assembly is operable to connect the sensing element to the control.

9. The surgical apparatus of claim 1, wherein the cable assembly further comprises:
a jack having a third housing with a cable portion extending from the third housing to the cable body,
wherein the third housing and the cable portion is separate from the second housing.

10. The surgical apparatus of claim 1, wherein the sensing element is a Hall Effect Sensor.

11. The surgical apparatus of claim 1, wherein the sensing element is a strain gauge.

12. The surgical apparatus of claim 1, wherein the sensing element is an inductive coupled circuit.

13. A surgical method, comprising:
connecting a first terminal end of a cable assembly to a handpiece having a first housing to be grasped by a user, wherein the first housing encloses at least a motor that is configured to operate a surgical tool received by the handpiece;
connecting a second terminal end of the cable assembly to a control separate from the handpiece, wherein the control is configured to receive a first position signal and generate a second control signal for the motor; and
manually moving a switch member moveably connected to a second housing of the cable assembly, wherein the switch member further comprises a signaling member fixed relative to the switch member and moveable with the switch member relative to a sensing element in the second housing, wherein the second housing has a wall surrounding at least a portion of at least a first electrical conductor and the sensing element, the second housing integrated with the cable assembly while configured to be selectively and removably connected to the handpiece;
wherein manually moving the switch member generates the first position signal that is transmitted to the control via the first electrical conductor extending through the second housing and along a cable body away from the second housing, wherein the first electrical conductor is configured to transmit the first position signal;
wherein the control generates the second control signal that is transmitted via the first electrical conductor extending through the second housing and along a cable body away from the second housing to the electrical motor within the handpiece.

14. The method of claim 13, further comprising:
connecting a surgical tool to the handpiece; and
manually operating the switch member to operate the surgical tool.

15. The method of claim 14, wherein manually moving the switch member, includes moving a magnet as the signaling member relative to a Hall effect sensor as the sensing element.

16. The method of claim 14, wherein manually moving the switch member, includes moving a spring as the signaling member relative to a strain gauge as the sensing element.

17. The method of claim 14, wherein manually moving the switch member, includes moving a first portion of an inductive coupled circuit as the signaling member relative to a second portion of an inductive coupled circuit as the sensing element.

18. The method of claim 13, further comprising:
disposing of the cable assembly that includes the switch member;
connecting a second cable assembly including a second switch member to the handpiece; and
operating the handpiece with the second cable assembly and second switch.

19. A surgical apparatus, comprising:
a handpiece having a first housing to be grasped by a user, wherein the first housing encloses at least a motor that is configured to operate a surgical tool received by the handpiece; and
a cable assembly configured to be selectively connected to the handpiece, the cable assembly further comprising:
a sensing element to generate a first position signal;
at least one electrical conductor configured to transmit the first position signal and a second control signal;
a second housing that houses at least a portion of the at least one electrical conductor and the sensing element, the second housing configured to be selectively and removably connected to the handpiece, wherein the at least one conductor extends through the second housing and along a cable body away from the second housing to a control, wherein the control is configured to receive the first position signal and generate the second control signal for the motor;
a switch assembly configured to be connected to and moveable relative the second housing to interact with the sensing element;
wherein the sensing element, surrounded by the second housing, is positioned between the motor in the handpiece and the control when the cable assembly is selectively connected to the handpiece and the control, wherein the sensing element is configured to generate the first position signal based at least on a position of the signaling member relative to the sensing element.

20. The surgical apparatus of claim 19, wherein the switch assembly of the cable assembly further comprises a signaling member fixed relative to the switch member and moveable with the switch member relative to the sensing element in the second housing.

21. The surgical apparatus of claim 19, wherein the switch assembly of the cable assembly further comprises a switch member configured to be moved by manual operation of the user.

22. The surgical apparatus of claim 21, wherein the switch member moves a signaling member relative to the sensing element and is connected to the second housing member.

23. The surgical apparatus of claim 22, wherein the sensing element is a Hall Effect Sensor.

24. The surgical apparatus of claim 22, wherein the sensing element is a strain gauge.

25. The surgical apparatus of claim 22, wherein the sensing element is an inductive coupled circuit.

26. The surgical apparatus of claim 19, further comprising:
the control spaced apart from the handpiece and configured to receive the first position signal and generate the second control signal for the motor.

* * * * *